United States Patent [19]

Spangler

[11] 4,311,669

[45] Jan. 19, 1982

[54] MEMBRANE INTERFACE FOR ION MOBILITY DETECTOR CELLS

[75] Inventor: Glenn E. Spangler, Baltimore, Md.

[73] Assignee: The Bendix Corporation, Southfield, Mich.

[21] Appl. No.: 180,219

[22] Filed: Aug. 21, 1980

[51] Int. Cl.³ .................. G01N 27/66; G01N 21/31
[52] U.S. Cl. .................................... 422/98; 23/232 C; 23/232 E; 422/83
[58] Field of Search .............. 422/98, 90, 83, 50; 23/232 E, 232 C, 232 R; 73/23, 23.1, 26; 204/195 R

[56] References Cited

U.S. PATENT DOCUMENTS

| | | | |
|---|---|---|---|
| 3,540,851 | 11/1970 | Vree et al. | 23/232 E |
| 3,589,869 | 6/1971 | Scolnick | 23/232 E |
| 4,261,698 | 4/1981 | Carr et al. | 23/232 E |

*Primary Examiner*—Ronald Serwin
*Attorney, Agent, or Firm*—W. G. Christoforo; Bruce L. Lamb

[57] ABSTRACT

A membrane interface is provided over the sample inlet port of an ion mobility detector. Sample, included as a vapor component in a gas stream impinging the exterior surface of the membrane, penetrates the membrane and is carried into the ion mobility detector by means of a carrier gas which scrubs the interior surface of the membrane.

7 Claims, 4 Drawing Figures

MEMBRANE INTERFACE FOR ION MOBILITY DETECTOR CELLS

FIELD OF THE INVENTION

This invention relates to ion mobility detectors and more particularly to means for improving the selectivity thereof through the use of a membrane interface for injecting a sample of the gas to be detected into the detector cell.

BACKGROUND OF THE INVENTION

Ion mobility detectors are the primary instruments used in the field of plasma chromatography. Generally, the operation of an ion mobility detector is similar to the operation of a time of flight mass spectrometer, the obvious difference being that a time of flight mass spectrometer operates in a vacuum where the mean free path of the contained gases is many times the dimensions of the gas container, while the ion mobility detector operates generally at atmospheric pressure where the mean free path of the contained gases is a small fraction of the dimensions of the container. More particularly, a typical ion mobility detector is comprised of a combined ionization source and an ion reaction region, an ion drift region and an ion injection shutter or grid interposed between the ion reaction region and the ion drift region. A carrier gas, normally purified air or nitrogen, is introduced into the ion mobility detector to transport sample vapor of a material, whose identity is to be characterized, into the ion mobility detector, so that the gaseous mixture is exposed to the ionization source. As a result, portions of both the carrier gas and the sample are directly ionized by the ionization source. However, as known to those practicing in this art, the characteristics of the carrier gas and the sample are usually such that the molecules of the carrier gas are more easily directly ionized by the ionization source than are the molecules of the sample. At this time the gaseous mixture is contained within the reaction region. Since the mean free path is many times smaller than the dimensions of the reaction region there are multiple collisions between the molecules of the carrier and sample gases. As also known to those skilled in the art, the tendency of these collisions is to transfer the ion charge from the carrier molecules to the sample molecules, thereby ionizing the sample gas mainly by this secondary ionization process.

The charged particles or ions, derived from both the sample and carrier gas, are accelerated to a terminal velocity under the influence of a field potential gradient within the reaction region toward an ion injection grid which, as mentioned earlier, separates the reaction region from the drift region. The grid is normally electrically biased to prevent the transfer of ions from the reaction region to the drift region. Periodically, the grid is deenergized for a short time period to permit a pulse of ions to pass therethrough into the drift region. Here, the ions, under the influence of an electrostatic drift field are drawn to an electrometer detector which terminates the drift region. The time of arrival of each ion at the electrometer detector, relative to the time the grid was opened, is determined by the ion's mobility through the non-ionized gas occupying the drift region. The heavier ions characteristically move more slowly through the drift region and arrive at the electrometer detector after longer drift times than lighter ions. It is thus possible to characterize the ions and hence, the sample by observing the time between the opening of the grid and the arrival of ions at the electrometer detector.

In a practical sense, an ion mobility detector may be used to determine whether a certain sample is present in an environment, such as a certain contaminant in atmospheric air. In this case the electrometer detector is sampled at predetermined times after the grid is opened to discover whether pulses of ions are then arriving at the electrometer detector. If electric current is measured then it can be concluded that the contaminant is present.

In the prior art, as mentioned above, the gaseous or vaporous sample, whose identity is to be characterized by the ion mobility detector, is injected or drawn into the reaction region to react with carrier gas ions formed therein by the ionization source. If it is desired to determine whether the atmosphere contains a certain component, usually a contaminant, the sample can simply be a sample of ambient air.

Several problems are encountered when using ion mobility detectors for environmental sampling purposes. A first problem involves no alarms due to interferences from the normal composition (e.g. oxygen, water, ammonia and/or nitrogen oxides) of the ambient air being drawn into the reaction region of the detector cell. The second involves false alarms or no alarms due to interferences from extraneous vapor components contained in the ambient air being drawn into the reactor region of the detector cell.

The first problem is associated with the principles underlying the tendency of a charge residing on a reactant ion to transfer to a neutral sample molecule. The transfer of the charge is necessary if a produce ion is to be formed from the sample molecule and the sample molecules are to be detected. As is known to those skilled in the art, this tendency to transfer charge is related to the relative proton and/or electron affinities of the ions and molecules present in the reactor region either due to composition of the carrier gas or to products of the ionization process. Since ammonia has a relatively high proton affinity and the oxides of nitrogen have high electron affinities, very few sample molecules can remove charge from these normal components of ambient air for ionization purposes. Examples include the inability to detect halogenated compounds in the presence of negative ions of nitrogen dioxide and to detect acids and alcohols in the presence of the positive ammonium ion. Hence, to allow ambient air sampling by an ion mobility detector, a means must be provided that will discriminate between the entrance of these normal components of ambient air and the sample molecules of interest into the ion mobility detector.

The second problem is associated not only with the principles underlying the tendency of a charge residing on a reactant ion to transfer to a neutral sample molecule, but also the probabilities associated with extraneous component vapors contained in ambient air having similar ion mobilities to the sample compound of interest. That is, if the environmental sample contains one or more extraneous components whose ion charge is the same as, and whose ion mobility is similar to, that of the sample it is desired to detect, then ions of the extraneous components will arrive at the electrometer detector at such a drift time as to indicate the looked for sample is present when in fact it may not be, thus causing a false indication or alarm. An aggravated example of this problem is the tendency of the normal alkanes to cluster into molecules or ions of larger mass and/or decompose into ions of lower mass so that the electrometer detector senses the arrival of ions with a wide range of drift times. That is, irrespective of the drift time for the sample molecule, an ion is formed from the normal alkanes whose mobility approximates that of the looked for sample molecule. This leads to a false indication or alarm as described above. Since a problem of this type is most severe for interferants at high concentration, a means must be provided that will discriminate between the entrance of these problem interferants and the sample molecules of interest into the ion mobility detector.

SUMMARY OF THE INVENTION

A membrane interface to the ion mobility detector provides this discrimination capability. Although a membrane interface to a mass spectrometer has previously been shown to be ideal for the separation of the high vacuum of the detector cell from the high pressure sample gas, no motivation has existed until now to use membrane interfaces for ion mobility detectors since ion mobility detectors normally operate under atmospheric or ambient pressure conditions, thus removing the requirement to preserve a vacuum. In addition, one might expect that such membranes would also be ineffective for ion mobility detectors as there is a large partial pressure differential across the membrane and thus the sensitivity of an ion mobility detector having a membrane interface would be degraded. The fact, however, that the partial pressure drop across a membrane can be made selective to specific compounds and can be reduced for other compounds makes a membrane interface to an ion mobility detector attractive. The achievement of selectivity is accomplished by a variety of membrane selection criteria. These include the selection of porous or non-porous type membranes or the use of these membranes with impregnants to enhance selective transmission of sample molecules through the membrane into the ion mobility detector by appropriate adjustment of solubility parameters for the membrane. That is, the properties of a membrane can be chemically adjusted so that a sample molecule approaching the membrane will more favorably dissolve in the membrane. Dissolution is required before a sample molecule can be transmitted through the membrane into the ion mobility detector.

The invention is embodied as a permeable membrane stretched over the sample input port of an ion mobility detector cell. A gaseous stream which may contain the sample in gaseous or vaporous state is caused to impinge on the exterior face, that is the face exterior to the detector cell, of the membrane. At the same time a carrier gas is caused to flow over the interior face of the membrane, so as to scour that face. The carrier gas then flows into the ion mobility detector reaction region. Sample molecules which permeate the membrane are thus immediately removed from the membrane inner face into the reaction region. This maintains the sample partial pressure at the membrane inner face low so as to improve sample permeation.

Other than as described immediately above, the construction and operation of the ion mobility detector can be entirely conventional.

The advantage of the invention is that an ion mobility detector of increased sensitivity and specificity is provided.

DESCRIPTION OF THE PREFERRED EMBODIMENT

Figure 1:
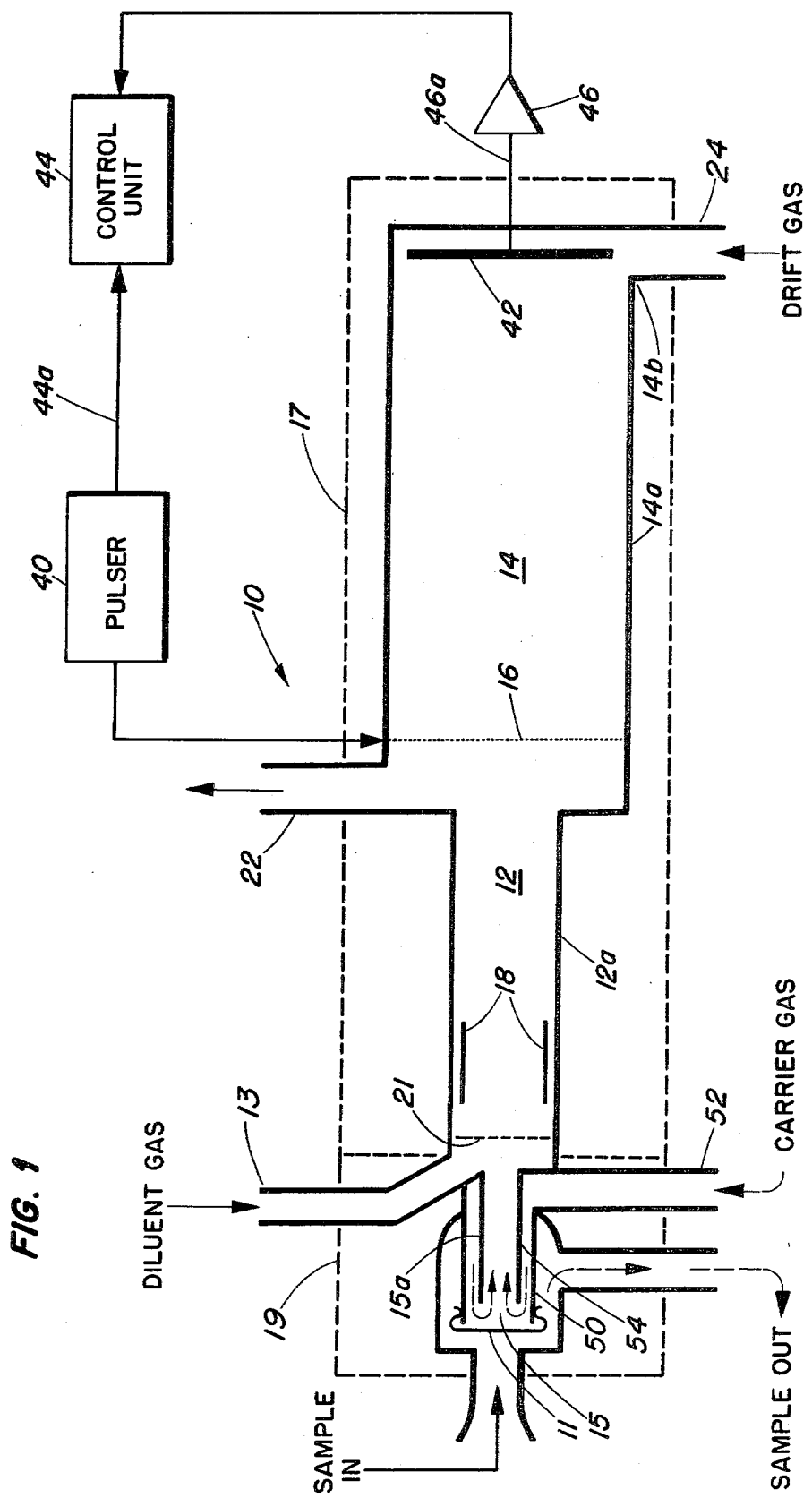
FIG. 1 is a diagrammatic longitudinal sectional view which illustrates an ion mobility detector employing the means of the present invention.

Referring first to FIG. 1, an ion mobility detector 10, typical except for having a membrane 11 stretched over its inlet port 15, is comprised of a reaction region 12, an ion drift region 14, an ion injector or shutter grid 16 located therebetween, and an ionization source 18. Dotted lines 17 and 19 represent an outer case for the ion mobility detector which encloses suitable heating means, not shown, to provide correct temperature for ion mobility detector operation. Dotted lines 19, in particular, represent an enclosure for the membrane heaters. Typically, a membrane such as a dimethysilicone membrane is operated at ion mobility detector cell temperature but also may be at a different temperature than cell temperature. Reaction region 12 and ion drift region are normally serially extended cylinders defined by tubes 12a and 14a respectively. A further cylindrical structure 15a concentric with cylinders 12a and 14a extends from the reaction region 12. Cylindrical structure 15a is open at one end to provide a sample inlet port 15 and is open at the other end into reaction region 12. The length of cylindrical structure 15a is kept relatively short and small in diameter to improve sample transmission characteristics.

In normal operation, that is without the means of the present invention and specifically without membrane 11, a gaseous mixture comprised of a carrier gas normally atmospheric air, and a sample of the gas or vapor which is to be characterized by the ion mobility detector, is injected through sample input port 15 into reaction region 12.

A diluent gas, suitably purified air or nitrogen, can optionally be injected into reaction region 12 through a diluent port 13 to dilute the concentration of sample molecules in the carrier gas mixture. A standard diffuser 21 is optionally provided at the entrance to reaction region 12 to ensure complete mixing of the carrier, diluent and sample.

Another inlet port 24 is provided at end 14b of drift region 14, through which is injected a drift gas, also suitably purified air or nitrogen, whose purpose will be explained below. A vent 22 is provided at the juncture of cylinders 12a and 14a from which the various gases are removed from the ion mobility detector.

The gaseous mixture injected into reaction region 12 passes in close proximity to an ionizer such as ionization source 18 which is suitably nickel 63, a source of beta particles. Other ionizers such as tritium or americium radioactive photoionization, or corona discharge sources might also be used. As known in the art, the beta particles primarily ionize the molecules of the carrier gas and the ionized carrier gas molecules ionize the sample molecules due to reactions and ion exchanges therebetween in the reaction region.

A voltage potential gradient is impressed along the length of the ion mobility detector from the diffuser 21 (which also acts as a repeller grid) to faraday cup 42 (by a means which is not shown), thus causing a field potential gradient in tube 12a which accelerates the ions toward ion injector grid 16. The non-ionized molecules are carried along toward grid 16 in the normal flow of gases toward vent 22. Since the ion mobility detector operates at or near atmospheric pressures, the mean free path of the ions and other molecules is very much less than the distance from diffuser 21 to grid 16. Thus, there are many collisions between the various gas molecules in reaction region 12. These collisions tend to create ionized sample molecules and deionize the previously ionized carrier gas molecules. The non-ionized molecules, mostly carrier gas molecules, are generally swept out of the ion mobility detector through vent 22, while the ionized molecules, a mixture of reactant and sample productions, are deionized on the reaction region side of grid 16, which is electrically biased by pulser 40 to prevent the passage of ions.

A control unit 44 includes an electronic clock which generates trigger pulses on line 44a which are applied to pulser 40. In response to a trigger pulse, pulser 40 generates a short pulse which is applied to grid 16 to bias the grid momentarily to allow a bundle of ions to pass through the grid from reaction region 12 into drift region 14.

The ions entering drift region 14 through grid 16 are accelerated toward faraday cup 42, in response to the aforementioned field gradient, in accordance with their mobility, the more mobile ions being accelerated faster and thus reaching faraday cup 42 before less mobile ions. The ions do not tend to fall into a continuous mobility spectrum but rather tend to fall into discrete mobility groups. Thus, groups or bundles of ions will reach faraday cup 42 at discrete times after grid 16 is pulsed on with the time being related to the mobility of the ions in the bundle. The ions are deionized by the faraday cup, thus generating an electrical current in line 46a whose magnitude is related to the number of ions instantaneously striking the faraday cup. This current is amplified by amplifier 46 and applied to control unit 44 where it is suitably displayed on a time base.

Not only are the ions of the sample and carrier passed through grid 16 into drift region 14, but also non-ionized molecules of sample and carrier continuously migrate into the drift region. Under these conditions further ionizing of non-ionized sample molecules might occur through collision of the sampe molecules with carrier ions in the drift region. Since this occurs some finite time after the original sample ions have been subject to the influence of the electrostatic drift field gradient, this subsequent generation of sample ions will result in a broadening or smearing of the ion mobility spectrum. The drift gas injected at port 24 hinders the formation of new sample ions in the drift region by sweeping non-ionized sample molecules out of the drift region and out through vent 22. In a practical ion mobility detector the volumetric flow of drift gas is several times the flow of the carrier and sample gaseous mixture.

More particularly, the volumetric flow of drift gas to carrier gas is in the same approximate relationship as the cross-sectional area of the drift region to that of the reaction region. In an actual ion mobility detector the cross-sectional area of the drift region was about three times that of the reaction region, with drift gas flow at 600–700 cubic centimeters per minute and carrier gas flow at 200–300 cubic centimeters per minute.

According to the present invention a second concentric cylinder 50 is provided around cylinder 15a at sample inlet port 15. Cylinder 50 is open-ended at inlet port 15 and permeable membrane 11 is stretched over this opening, thus providing a membrane interface at inlet port 15 between the ion mobility detector and the sample source. A port 52 communicates carrier gas to the space 54 between cylinders 15a and 50. Carrier gas thus flows in the direction of the various carrier gas arrows in space 54 to impinge on the inner face of membrane 11 so as to scour that face as the carrier gas flows into reaction region 12.

The sample gas or vapor is caused to flow in the direction of the sample arrows so as to impinge on the exterior face of membrane 11. Molecules of the sample permeate the membrane into the carrier gas to be thus swept into reaction region 12. The amount or yield of sample entering the carrier gas is directly proportional to the partial pressure gradient of sample across the membrane, between the exterior and interior faces thereof, and inversely proportional to the carrier gas flow rate.

Two types of membranes have been tested on ion mobility detectors and found to operate satisfactorily. These are the non-porous semipermeable type membranes such as dimethylsilicone, dimethyl polysiloxane, copolymers of dimethysilicone and polycarbonate, dimethyl-methy vinyl polysiloxane, etc. which depend on the solubility of the sample in the membrane for sample transport purposes, and the porous diffusion type membranes such as microporous TFE and microporous polypropylene, which depend upon Knudsen diffusion for sample transport. Both types of membranes can be impregnated with reagents such as might be commonly used as liquid phases in the field of gas liquid chromatography to alter the solubility of nonporous membranes and to convert porous membranes to nonporous membranes. The yield, Y, is given by:

$$Y = \frac{P_2}{P_1} = \frac{P_r A_m P_t}{Q_c l + P_r A_m P_t}$$

where:
$P_1$ is the sample partial pressure at the membrane exterior face,
$P_2$ is the sample partial pressure at the membrane interior face,
$P_r$ is the membrane permeability coefficient,
$A_m$ is the membrane area,
$Q_c$ is the volumetric flow of carrier gas,
l is the membrane thickness and
$P_t$ is total pressure.
For non-porous membranes:
$P_r = DS$
D = Diffusion of vapor through membrane
S = Solubility of vapor in membrane.
For porous membranes:
$P_r = \epsilon T_R D_{kA}/P_R T$
$\epsilon$ = geometric term including parameters such as porosity and tortuosity
$T_R$ = room temperature
$P_R$ = atmospheric pressure
T = membrane temperature
$D_{kA}$ = Knudsen diffusion coefficient given by
$D_{KA} = \frac{2}{3}r(8RT/\pi M_\omega)^{\frac{1}{2}}$ r = radii of pore
R = Gas constant
$M_\omega$ = molecular weight of diffusing vapor.

Figure 2:
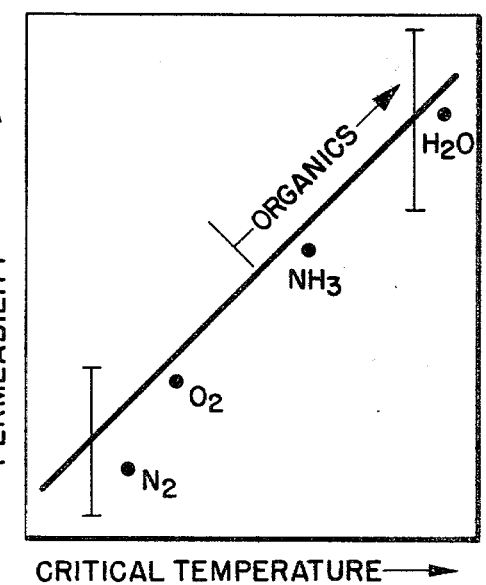
FIG. 2 is a graph of the permeability of various molecules through a nonporous dimethysilicone membrane.

Generally, the teachings as to membrane materials and thicknesses and the theory of sample penetration found in the various publications devoted to the field solution chemistry, diffusion theory and/or polymer science are applicable to the present invention. More specifically, polymer and non-porous impregnated membranes suitable for use with this invention are characterized by generally being free of holes. Sample molecules can pass through such materials only by diffusion. However, in order to diffuse through the membrane, the sample material must first be captured by the membrane either by entering into solution therewith or adhering thereto. Although most gases can be captured by such membrane materials, the permanent gases generally will not be efficiently captured at elevated temperatures, that is, at temperatures substantially above zero degrees Celsius. Further, the ability of a membrane to pass molecules onto the ion mobility detector is related to its permeability. The greater the permeability of the membrane to a selected molecule the greater the transmission of that molecule through the membrane. The lesser the permeability of the membrane to a particular molecule the lesser the transmission. A graph of molecule permeability through dimethylsilicone membranes is shown at FIG. 2 where permeability is plotted on a logarithmic scale against critical temperature. As can be seen, permeability of a particular material is related generally to the critical temperature of that material. It is interesting to note that the permanent gases have generally low permeability. It is also interesting to note that ammonia, $NH_3$, also has a relatively low permeability. Since ammonia is usually present in ambient air and because of its high proton affinity it is a major interferent in ion mobility detection, the fact that it can be excluded by a dimethylsilicone membrane when the ion mobility detector is being used to detect the higher permeable organic compounds, is a major advantage of using such a membrane at the ion mobility interface.

Figure 3:
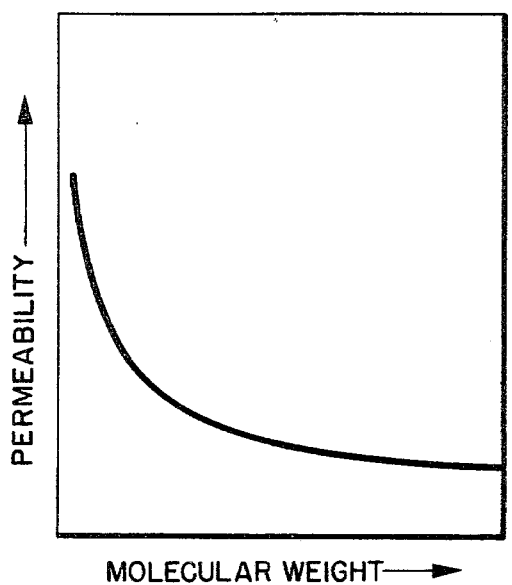
FIG. 3 is a graph of the permeability of molecules through a general porous membrane.

Conversely, selectivity toward atmospheric ammonia or nitrogen dioxide can be accomplished with a porous membrane material, such as microporous polypropylene, microporous teflon, etc., which displays enhanced permeability to these molecules relative to the organics. More particularly, the porous membrane materials exhibit a permeability vs. molecular weight of sample such as that of FIG. 3 which, it can be seen, is nearly the reverse of that of the non-porous membrane materials.

Figure 4:
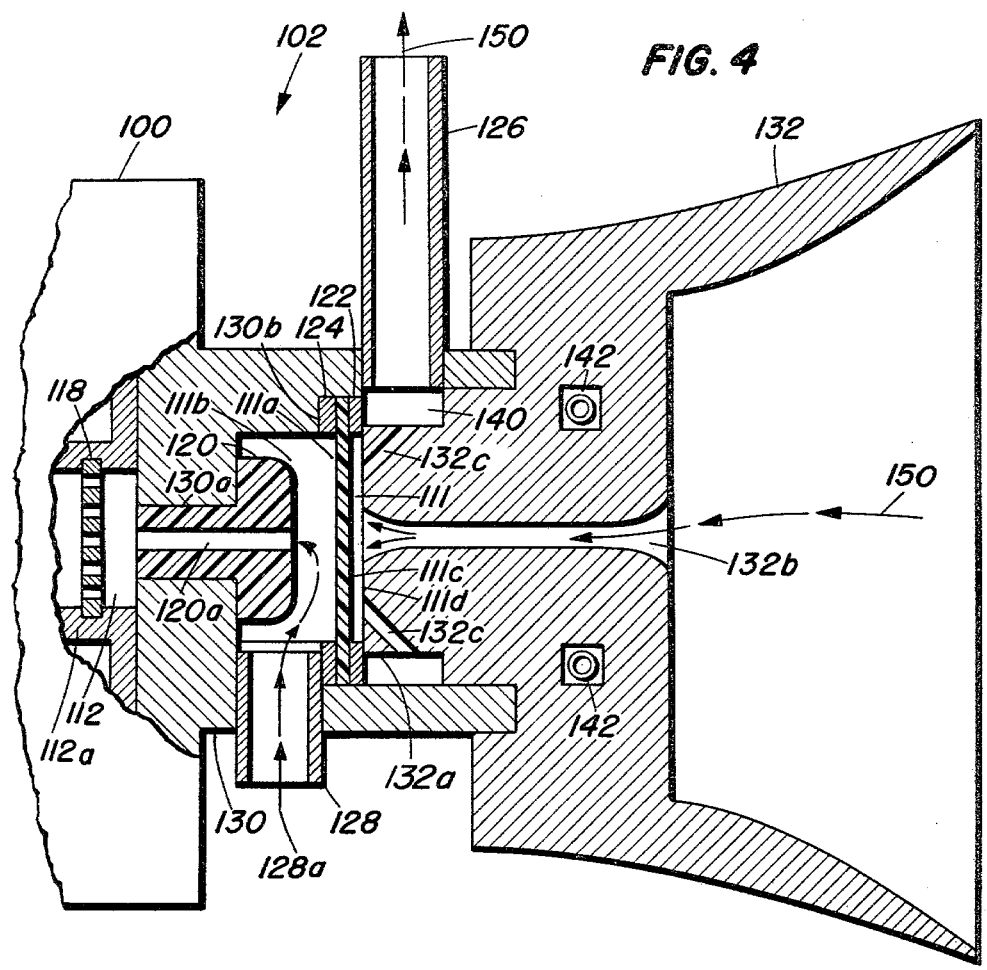
FIG. 4 is a longitudinal sectional view which illustrates a form of the invention in greater detail.

Refer now to FIG. 4 where an ion mobility detector membrane interface is shown in greater detail. There is shown the sample inlet end 100 of an ion mobility detector broken away to show the membrane interface 102. In particular, the input end 112 of the reaction region defined by cylinder 112a is shown in which is located a standard diffuser 118. The membrane interface is comprised of mushroom-shaped port orifice member 120 having a central orifice 120a of narrow bore which communicates the interior face 111a of membrane 111 and more particularly the interior volume 111b with reaction region 112. Port orifice member 120, which is suitably teflon (TFE), is supported in bore 130a of the generally cylindrical port support member 130 which also supports sample suction port 126 and carrier gas supply port 128. The latter port also communicates with interior volume 111b and carrier gas is injected therethrough to flow in the direction of arrows 128a to scour the interior face 111a of membrane 111 and thence through bore 120a into reaction region 112. Generally, membranes are about one mil thick.

Membrane 111 together with membrane support rings 122 and 124 make up the membrane means which is held and sealed at its periphery between shoulder 130b of port support member 130 and port venturi member 132. Member 132 has a venturi-shaped central bore 132b which communicates the sample source, usually atmospheric air, with the membrane exterior face 111c and more particularly with exterior volume 111d. Exterior volume 111d also communicates through the obliquely slanted passages 132c in end 132a of member 132 to annular volume 140. This later volume communicates with sample suction port 126. Suction at this port causes the sample to be drawn in accordance with arrows 150 through venturi 132b to impinge on exterior face 111c of membrane 111. Heaters 142 are imbedded in the venturi port member to allow thermostat control of the temperature of the membrane and inlet system.

Various alterations and modifications of this invention should now be obvious to one skilled in the art after a reading and understanding of the foregoing. It is thus intended that the invention be limited only by the true spirit and scope of the appended claims.

The invention claimed is:

1. In an ion mobility detector wherein a sample gas or vapor and carrier gas are injected into a reaction region thereof, a membrane interface separating the sample source from the carrier gas comprising:
    a membrane having a face exterior to said ion mobility detector in communication with said sample source and an interior face which communicates with said reaction region; and,
    passage means for injecting said carrier gas onto said interior face and thence into said reaction region.

2. The membrane interface of claim 1 wherein said membrane is a nonporous membrane.

3. The membrane interface of claim 2 wherein said membrane is made of material chosen from the group which includes dimethyl-silicone, dimethyl polysiloxane, copolymers of dimethysilicone and polycarbonate, and dimethyl-methyl vinyl polysiloxane.

4. The membrane interface of claim 1 wherein said membrane is a porous membrane.

5. The membrane interface of claim 4 wherein said membrane is chosen from the group which includes microporous TFE and microporous polypropylene.

6. The membrane interface of claim 1 including second passage means injecting said sample onto said exterior face.

7. The membrane interface of claim 2 or 4 wherein said membrane is impregnated with a liquid phase reagent.

* * * * *